United States Patent [19]

Fujiyama et al.

[11] Patent Number: 4,514,563
[45] Date of Patent: Apr. 30, 1985

[54] HIGHLY VISCOUS POLYSACCHARIDES

[75] Inventors: Seiichi Fujiyama; Hiroyuki Minakami, both of Aichi; Hiroshi Masai, Hanada, all of Japan

[73] Assignee: Nakano Vinegar Co., Ltd., Handa, Japan

[21] Appl. No.: 479,919

[22] Filed: Mar. 29, 1983

Related U.S. Application Data

[63] Continuation-in-part of Ser. No. 436,398, Oct. 25, 1982, abandoned.

[30] Foreign Application Priority Data

Nov. 5, 1981 [JP] Japan .................... 56-176510

[51] Int. Cl.$^3$ .................... C08B 37/00; C12P 19/06
[52] U.S. Cl. .................... 536/123; 435/101; 536/114
[58] Field of Search .................... 536/123, 114

[56] References Cited

U.S. PATENT DOCUMENTS 4,211,774 7/1980 Kang et al. .................... 536/123
4,329,448 5/1982 Cox et al. .................... 536/123

OTHER PUBLICATIONS

Choy et al., "Can. Jour. of Chem.", vol. 51, 1973, pp. 198-207.
Kelco, "Xanthan Gum" 2nd Ed.

*Primary Examiner*—Johnnie R. Brown
*Attorney, Agent, or Firm*—Frishauf, Holtz, Goodman & Woodward

[57] ABSTRACT

Novel highly viscous polysaccharides composed mainly of (a) glucose, (b) galactose, (c) mannose, and (d) glucuronic acid, the molar ratio of (a):(b):(c):(d) being 10:3–6:0.5–2:0.5–2 (preferably 10:3–4:1–2:1–2). The invention also provides the process for producing the highly viscous polysaccharides which comprises cultivating a highly viscous polysaccharide-producing microorganism which is an acetic acid bacteria in a nutrient medium until a substantial amount of polysaccharides has accumulated in the nutrient medium, and recovering the accumulated polysaccharides from the nutrient medium.

3 Claims, 7 Drawing Figures

HIGHLY VISCOUS POLYSACCHARIDES

This application is a continuation-in-part, of application Ser. No. 436,398, filed Oct. 25, 1982, now abandoned.

BACKGROUND OF THE INVENTION

1. Field of the Invention

The present invention relates to novel polysaccharides having high viscosity and a process for the preparation of said polysaccharides.

2. Description of the Prior Art

Viscous polysaccharides have many applications in view of their properties such as adhesiveness and viscousness. There have been developed many applications for them, e.g., additives for foodstuffs and cosmetics, adhesives, coating agents, freeze stabilizers, lubricants, additives for drilling mud, and agents for use in the enhanced recovery of oil from oil fields. In recent years, it has been found that certain polysaccharides have pharmaceutical activity, such as an antitumor activity and a blood pressure-controlling action. It is therefore expected that their applications as medicines will increase.

SUMMARY OF THE INVENTION

The invention provides highly viscous polysaccharides by microbiological processes. It has been discovered that acetic acid bacteria isolated from a fermenting broth of vinegars are able to produce novel highly viscous polysaccharides which are composed mainly of (a) glucose, (b) galactose, (c) mannose, and (d) glucuronic acid, the molar ratio of (a):(b):(c):(d) is 10:3–6:0.5–2:0.5–2, and a process for the preparation of such highly viscous polysaccharides.

The structure of the main repeating units of the polysaccharide follows:

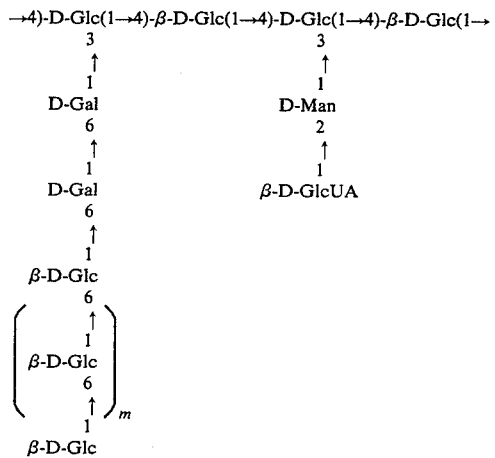

m is 0 or 1 (m on different side chains may be the same or different); Glc is glucose; Gal is galactose; Man is mannose; and GlcUA is glucuronic acid.

The back bone chain of the polysaccharide of the present invention is 1,4-D-glucan primarily containing the β-form of linkage. Two different side chains are attached at the C-3 position of the D-glucose residue of the back bone chain. The respective side chains have the following structures. (1) β-D-glucosyl-(1→6)-β-D-glucosyl-(1→6)-β-D-glucosyl-(1→6)-D-galactosyl-(1→6)-D-galactosyl-(1→ with m being 0 or 1, and (2) β-D-glucuronosyl-(1→2)-D-mannosyl-(1→. The respective branch points are at the alternate D-glucose residues of the back bone chain.

DETAILED DESCRIPTION OF THE INVENTION

Figure 1:
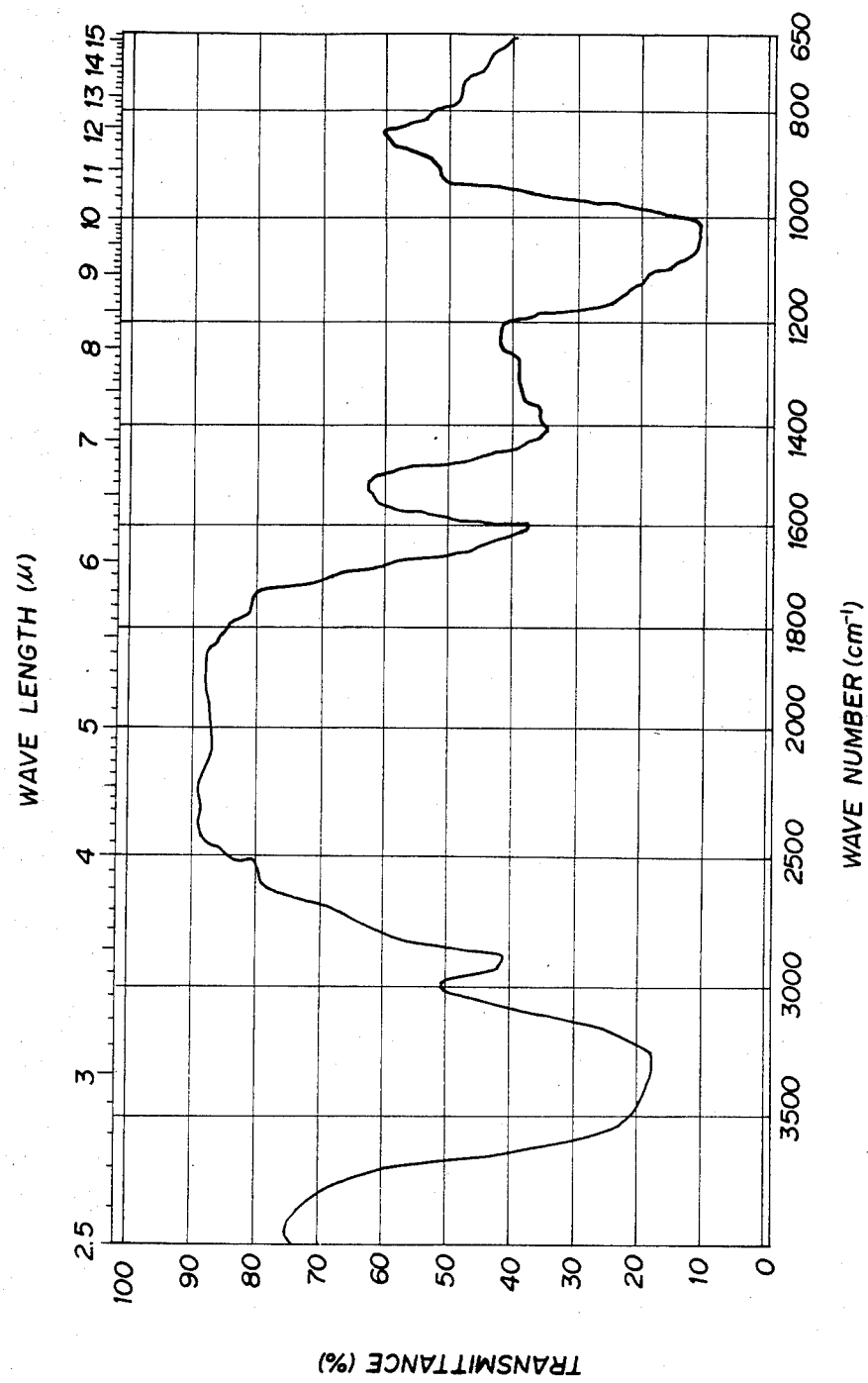
FIG. 1 is an infrared absorption spectrum of the polysaccharides of the invention before de-salting.

The polysaccharides of the invention can be prepared by the following method:

Microorganisms which are acetic acid bacteria and have the ability to produce the aforedescribed high viscous polysaccharides are cultivated in a nutrient medium until substantial amounts of the desired polysaccharides are accumulated, and the thus-accumulated polysaccharides are recovered from the culture broth.

Microorganisms which can be used in the preparation of the polysaccharides of the invention are acetic acid bacteria, including bacteria newly isolated from nature and bacteria available from institutes where microorganisms are deposited. In addition, artificially or naturally produced mutants can be used as long as they have the ability to produce the above-described polysaccharides.

Examples of microorganisms which can be used in the method of this invention are *Acetobacter polysaccharogenes* MT-11-2 and MF-8, which have been newly isolated from a fermenting broth of vinegars. In addition, *Gluconobacter capsulatus* IFO 3462 (NRRL B-1225), *Acetobacter pasteurianus* IFO 13751 (ATCC 23753), etc. can be used in the invention.

The microbiological characteristics of MT-11-2 and MF-8 are described hereinafter (which are common to both MT-11-2 and MF-8 unless specified separately for them).

The microbiological characteristics were investigated according to "Classification and Identification of Microorganisms", Tokyo University Press, Tokyo (June 20, 1975), "The Flagellation and Taxonomy of Genera Gluconobacter and Acetobacter with Reference to the Existence of Intermediate Strains" in The Journal of General and Applied Microbiology, Vol. 10, No. 2, pp. 95–126 (1964), and "Methods for Identifying Acetic Acid Bacteria" in "Identification Methods for Microbiologists", pp. 1–8 in The Society for Applied Bacteriology Technical Series No. 2 (1968).

The yeast extract-glucose-agar medium was prepared by dissolving 5 grams of yeast extract, 30 grams of glucose, 3 grams of polypeptone, and 15 grams of agar in 1 liter of distilled water and adjusting the pH to 6.5.

The yeast extract-glucose-liquid medium was prepared by dissolving 5 grams of yeast extract, 30 grams of glucose and 3 grams of polypeptone in 1 liter of distilled water and adjusting to pH 6.5.

The ethanol-containing yeast extract-glucose-liquid medium was prepared by dissolving 5 grams of yeast extract, 30 grams of glucose, and 3 grams of polypeptone in 1 liter of distilled water, adjusting to pH 6.5, and, after sterilization, aseptically adding 3% (V/V) of ethanol.

The MY plate medium was prepared by dissolving 10 grams of glucose, 5 grams of polypeptone, 3 grams of yeast extract, 3 grams of malt extract, and 15 grams of agar in 1 liter of distilled water and adjusting the pH to 6.5.

The bouillon liquid medium was prepared by dissolving 10 grams of meat extract, and 10 grams of polypeptone in 1 liter of distilled water, and adjusting to pH 6.5.

The sugar-added bouillon liquid medium was prepared by dissolving 10 grams of glucose, 10 grams of meat extract, and 10 grams of polypeptone in 1 liter of distilled water and adjusting to pH 6.5.

Identification of ubiquinone was performed by paper chromatography, thin-layer chromatography, infrared and ultraviolet photometry, and a mass analytical method.

(I) Morphological Characteristics

Shape: short rod
Size: 0.5–0.7 μm × 1.0–1.2 μm
Colony: single or chain
Motility: none
Spore: not formed
Gram staining: negative
Acid fastness: negative (II) Cultural Characteristics (1) Yeast Extract-Glucose-Agar Plate Culture (at 30° C. for 4 days)
    Shape: circular
    Edge: smooth and entire margin
    Projections: raised
    Gloss: lustrous
    Surface: smooth
    Color Tone: light yellow and lustrous for MT-11-2, and pale pink and lustrous for MF-8.

(2) Calcium Carbonate-Containing Yeast Extract-Glucose Slant Culture (at 30° C. for 3 days)
    Growth: good
    Projection: moderate
    Surface: smooth
    Edge: smooth and entire margin
    Color Tone: light yellow and lustrous for MT-11-2, and pale pink and lustrous for MF-8.

(3) Ethanol-Containing Yeast Extract-Glucose Liquid Stationary Culture (at 30° C. for 4 days)
    Fair growth. Moist and weak pellicle is formed.
    Turbid and a partial sedimentation on the bottom. No lethern sheet comprising cellulose is formed.

(4) Bouillon Liquid Stationary Culture (at 30° C. for 7 days)
    Scant growth. No lethern sheet comprising cellulose is formed. Growth in a ring-like form for MT-11-2, and for MF-8, a very thin pellicle is formed.

(5) Glucose-Containing Meat Extract Liquid Stationary Culture (at 30° for 7 days)
    Fair growth. No lethern sheet comprising cellulose is formed. For MT-11-2, the broth becomes turbid with a partial sedimentation, and a thin pellicle is formed. For MF-8, the broth becomes very turbid with sedimentation, and a weak pellicle is formed.

(6) MY Gelatin Hight-Layer Culture (at 20° C. for 7 days)
    Fair growth, and no liquefaction.

(7) Litmus Milk (at 30° C. for 7 days)
    No coagulation (III) Physiological Characteristics (1) Nitrate reduction: negative
(2) Denitrification: negative
(3) VP Test: negative
(4) Formation of Indole: negative
(5) Formation of Hydrogen Sulfide: negative
(6) Hydrolysis of Starch: negative
(7) Availability of Citric Acid: negative in a Christensen's medium
(8) Availability of Inorganic Nitrogen Sources: Nitrates: negative Ammonium Salts: negative
(9) Formation of Pigment into Medium: negative
(10) Urease: negative Oxidase: negative
(11) Catalase: positive
(12) Growth pH: 3.0 to 7.5 Optimum pH: 4.0 to 5.5
(13) Growth Temperature: 15° to 35° C. Optimum Temperature: 20° to 28° C.
(14) Attitude toward Oxygen: aerobic
(15) Formation of 5-Ketogluconic Acid: positive
(16) Formation of Dihydroxyacetone: positive
(17) Assimilation of Ethanol: Weakly assimilates ethanol, forming acetic acid.
(18) Assimilation of Acetic Acid: negative
(19) Assimilation of Lactic Acid: negative
(20) Requirement of Vitamins: positive
(21) Decomposition of Acetic Acid: positive
(22) Decomposition of Lactic Acid: positive
(23) Reaction to Ferric Chloride Test: negative (in a glucose medium)

(IV) Assimilation of Carbon Sources and Formation of Acids and Gases

As shown in Table 1.

TABLE 1

| Carbon Source | Assimilation | | Formation of Acids | | Formation of Gases | |
| --- | --- | --- | --- | --- | --- | --- |
| | MT-11-2 | MF-8 | MT-11-2 | MF-8 | MT-11-2 | MF-8 |
| L-Arabinose | ++ | ++ | ± | ± | − | − |
| D-Xylose | + | ± | + | + | − | − |
| D-Glucose | ++ | ++ | + | + | − | − |
| D-Mannose | ++ | + | − | − | − | − |
| D-Fructose | ++ | + | − | − | − | − |
| D-Galactose | ++ | + | + | + | − | − |
| Maltose | + | + | − | − | − | − |
| Sucrose | +++ | ++ | − | ± | − | − |
| Lactose | − | − | − | − | − | − |
| Trehalose | + | ± | − | − | − | − |
| D-Sorbitol | ++ | − | − | − | − | − |
| D-Mannitol | ++ | ++ | − | − | − | − |
| Inositol | − | − | − | − | − | − |
| Glycerin | + | + | − | ± | − | − |
| Starch | − | − | − | − | − | − |
| Ethanol | ± | ± | + | + | − | − |
| Propanol | − | − | + | + | − | − |
| Butanol | − | − | + | + | − | − |

TABLE 1-continued

| Carbon Source | Assimilation | | Formation of Acids | | Formation of Gases | |
|---|---|---|---|---|---|---|
| | MT-11-2 | MF-8 | MT-11-2 | MF-8 | MT-11-2 | MF-8 |
| Methanol | — | — | — | — | — | — |

Note:
+: assimilated or formed
++: well assimilated or formed
+++: very well assimilated or formed
—: not assimilated or formed
±: slightly assimilated or formed (V) Type of Coenzyme of Electron Transfer System
Main Component of Coenzyme: Ubiquinone-10

Based on the above-described characteristics, the taxonomic positions of the bacteria of the invention have been determined according to Bergey's "Manual of Determinative Bacteriology", 8th ed., "The Journal of General and Applied Microbiology", Vol. 10, pp. 95–126, "The Flagellation and Taxomony of Genera Gluconobacter and Acetobacter with Reference to the Existence of Intermediate Strains", and ibid., Vol. 15, pp. 181–196 (1969) "Enzymatic Studies on the Oxidation of Sugar and Sugar Alcohol, V, Ubiquinone of Acetic Acid Bacteria and its Relation to Classification of Genera Gluconobacter and Acetobacter, especially of the so-called Intermediate Strains".

In view of the fact that the present bacteria are Gram-negative aerobic bacilli which oxidize ethanol to form acetic acid and are capable of growing even at pH 3.0, it is clear that they belong to the genus Acetobacter or the genus Gluconobacter and generally referred to as acetic acid bacteria.

The present bacteria are considered to belong to the genus Gluconobacter in that the main ubiquinone type is $Q_{10}$, vitamins are essential for their growth, and they have dihydroxyacetone-producing ability. However, they have acetic acid and lactic acid-decomposing properties. In this respect, they are considered to belong to the genus Acetobacter. It is therefore very difficult to determine to which of the genus Acctobacter and the genus Gluconobacter the bacteria of the invention belong. In view of the fact, however, that they have acetic acid and lactic acid-decomposing properties, and have an ability to produce high viscous polysaccharides composed mainly of glucose, galactose, mannose, and glucuronic acid, it is believed reasonable to conclude that the present bacteria are novel strains belonging to the genus Acetobacter. Thus, the bacteria of the invention have been named "Acetobacter polysaccharogenes".

The above-described strains MT-11-2 and MF-8 are different with respect to the color tone in the yeast extract-glucose medium and the assimilation of sorbitol, although they have many similar properties, and they have been named "Acetobacter polysaccharogenes MT-11-2" and "Acetobacter polysaccharogenes MF-8", respectively. These Acetobacter polysaccharogenes MT-11-2 and Acetobacter polysaccharogenes MF-8 have been deposited in the Fermentation Research Institute, Agency of Industrial Science and Technology, Ministry of International Trade and Industry of Japan under the accession numbers of FERM BP-112 and FERM BP-113, respectively.

It is to be noted that, in addition to Acetobacter polysaccharogenes MT-11-2 and Acetobacter polysaccharogenes MF-8, other microorganisms classified as acetic acid bacteria can be used in the invention, as long as they produce the above-described acidic heteropolysaccharide. For example, Gluconobacter capsulatus IFO 3462 (NRRL B-1225), Acetobacter pasteurianus IFO 13751 (ATCC 23753), etc. can be used in the invention. However, in our experiment, Acetobacter aceti IFO 13752 (ATCC 12876), Acetobacter aceti ATCC 15973, Gluconobacter suboxydans ATCC 23652, etc. were recognized not to produce the above described acidic heteropolysaccharide.

Carbon sources which can be used in the invention include glucose, galactose, fructose, sucrose, glycerol, mannitol, ethanol, citric acid, malic acid, molasses, and saccharified liquids of various starch-containing cereals. These substances can be used alone or in combination with each other.

Nitrogen sources which can be used in the invention include organic and inorganic nitrogen sources, such as yeast extract, peptone, corn steep liquor, and ammonium sulfate.

Addition of small amounts of salts of potassium, calcium, magnesium, sodium, etc., and pantothenic acid, nicotinic acid, iron (Fe), cobalt (Co), molybdenum (Mo), etc. are effective for increasing the production of the above-described acidic heteropolysaccharides and the viscosity thereof.

Cultivation is performed in a medium having a pH of from 3 to 8, preferably from 5 to 7 at a temperature of from 20° to 35° C., preferably from 25° to 28° C. under aerobic conditions, usually by either shake culture or culture under aeration and agitation. The fermentation is usually performed for 24 to 96 hours.

The acidic heteropolysaccharides accumulated in the culture medium are recovered by known techniques. For example, the fermentation broth is subjected to a separation treatment such as centrifugal separation and filtration as such, or after being diluted with a suitable amount of water to separate microbial cells and any solid materials, and a precipitant, such as methanol, ethanol, propanol, and acetone, is added to the above-obtained filtrate to precipitate fibrous polysaccharides. These polysaccharides are collected, washed with acetone, and dried.

The polysaccharides are acidic substance and therefore they also can be recovered by the method comprising adding cetyltrimethylammonium bromide, for example, to the fermentation broth which has been freed of microbial cells.

The thus-obtained crude polysaccharides can be purified by techniques usually employed in the purification of polysaccharides. For example, by repeating a procedure comprising re-dissolving the polysaccharides in water, subjecting the resulting solution to a heat treatment and then to centrifugal separation to completely remove insoluble materials, and adding a precipitant, such as acetone, to the resulting filtrate to re-precipitate the polysaccharides, there can be obtained highly purified polysaccharides, which are white and in a cotton-like form. Furthermore, the highly purified products can be obtained by using a precipitation treatment using cetyltrimethylammonium bromide (CTAB treatment), dialysis, a treatment using an ion exchange resin, etc., in combination with each other.

The physical and chemical characteristics of the polysaccharides of the invention are as follows:

(1) Infrared Absorption Spectrum

Figure 2:
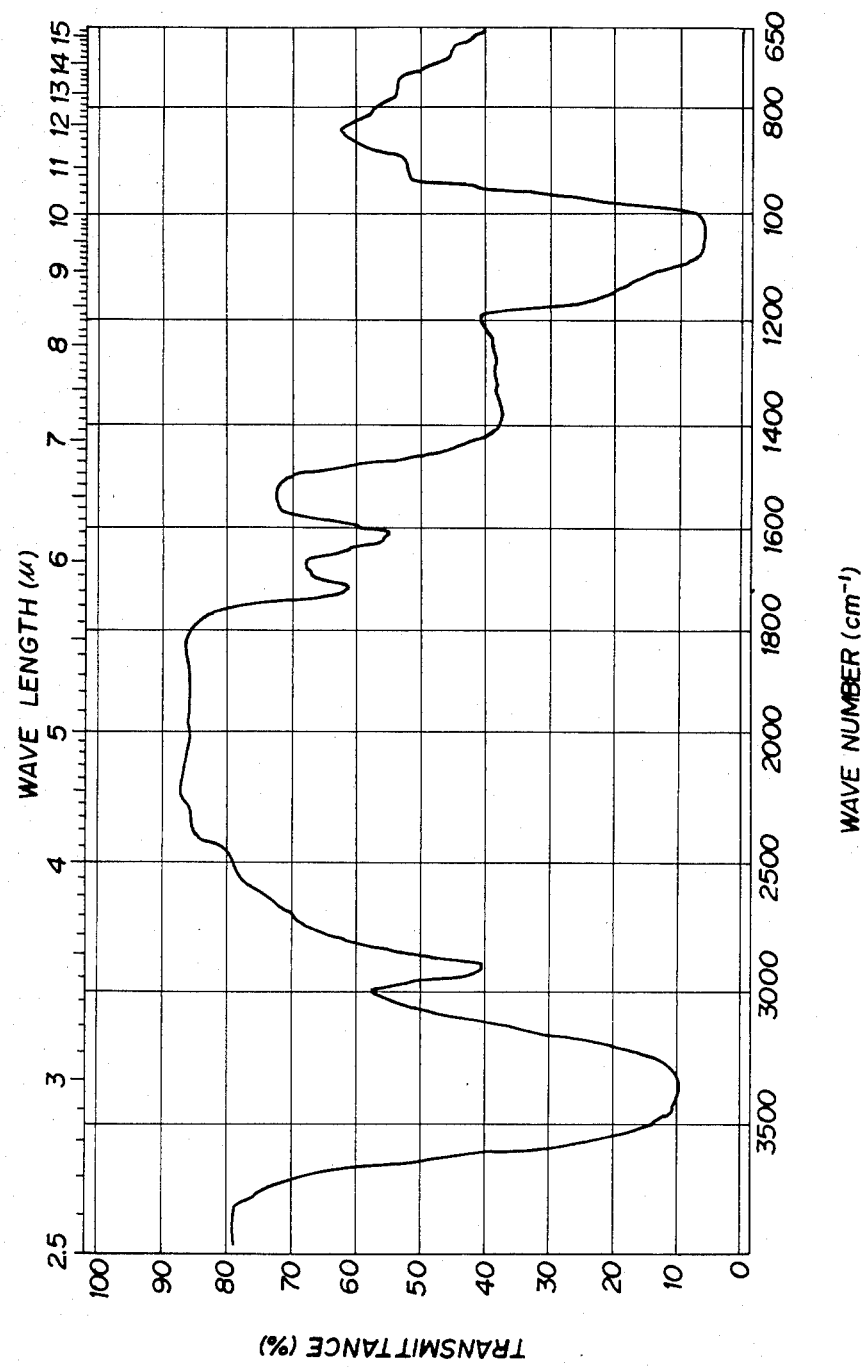
FIG. 2 is an infrared absorption spectrum of the polysaccharides of the invention after de-salting.

The infrared absorption spectrum of the polysaccharides before de-salting is shown in FIG. 1, and the infrared absorption spectrum after de-salting is as shown in FIG. 2.

(2) Color Reactions

Anthrone reaction: positive
Carbazole reaction: positive
Elson-Morgan reaction: negative
Iodo reaction: positive (3) Property (basic, acidic, or neutral)

White precipitates are formed on addition of cetyltrimethylammonium bromide or cetylpyridium chloride. Therefore, the present polysaccharides are acidic.

(4) Solubility

Soluble in water, and insoluble in methanol, ethanol, propanol, ether, acetone.

(5) Color and Appearance

The purified polysaccharides are white and in a cottonlike or fibrous form.

(6) Viscosity

The aqueous solution is colorless, transparent, and viscous. The viscosity of a 1% aqueous solution of the polysaccharides is 500–1,200 centipoises as determined by means of a Brookfield type viscometer (produced by Tokyo Keiki Co., Ltd., Japan) at a temperature of 25° C. and a rate of 30 revolutions per minute (rpm).

Figure 3:
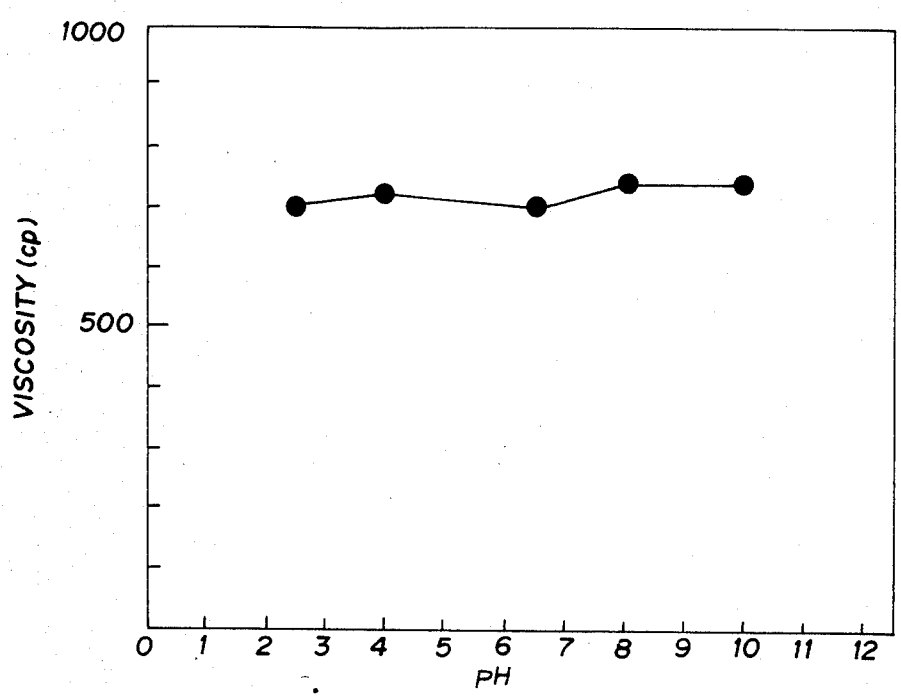
FIG. 3 is a graph showing the relation between viscosity of the polysaccharides of the invention and pH.

The influence of pH on the viscosity of the polysaccharides is shown in FIG. 3. From FIG. 3, there are observed no changes in viscosity with pH. In this experiment, a 1% (weight by volume (w/v)) solution was used as a sample.

Figure 4:
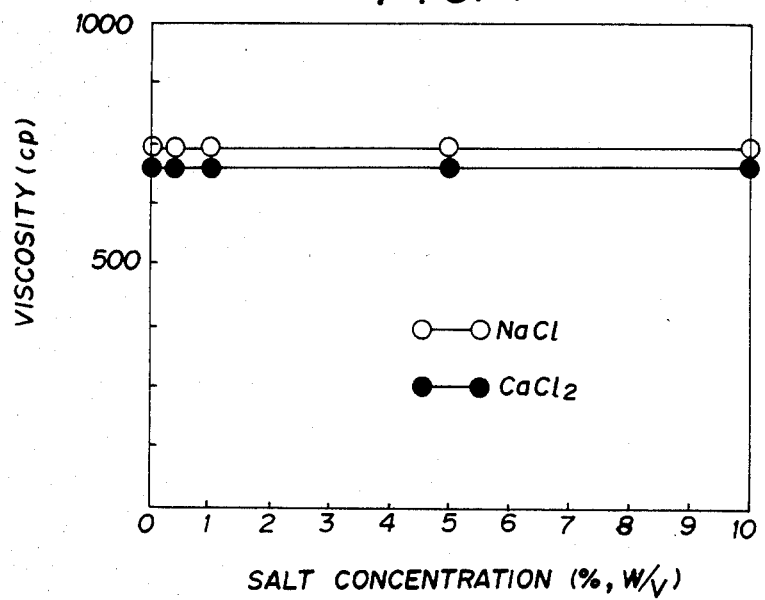
FIG. 4 is a graph showing the relation between viscosity of the polysaccharides of the invention and salt concentration.

FIG. 4 shows the influence of calcium chloride and sodium chloride on the viscosity of the polysaccharides. As apparent from FIG. 4, the polysaccharides of the invention are stable against divalent and univalent cations.

Figure 5:
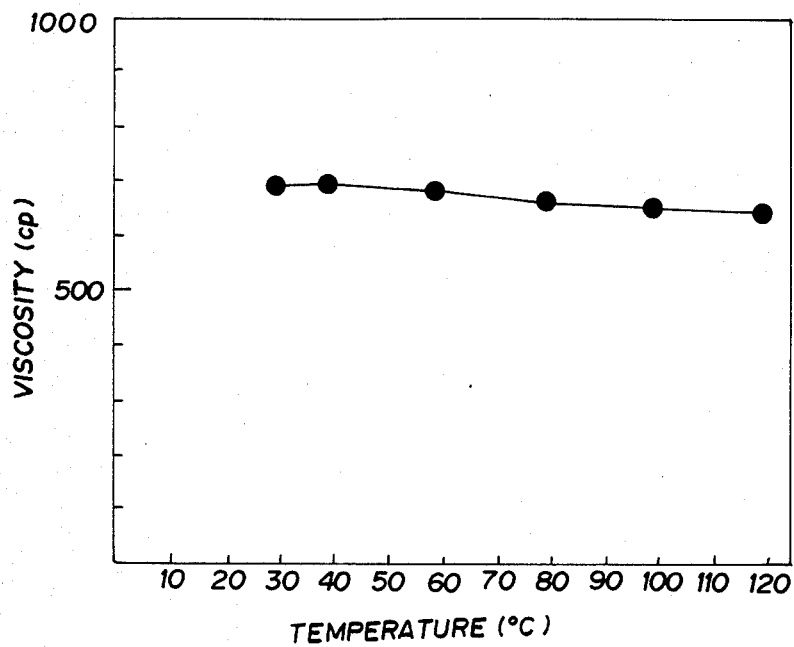
FIG. 5 is a graph showing the relation between viscosity of the polysaccharides of the invention and temperature.

FIG. 5 shows the heat stability of the polysaccharides of the invention. No significant changes in viscosity are observed for temperature changes ranging between 30° C. and 120° C..

(7) Main Constituents and Their Constitutional Ratio

When the polysaccharides of the invention are hydrolyzed with 2N sulfuric acid at 100° C. for 4 hours, and the hydrolyzed product was applied to thin-layer chromatography and developed with acetone, isopropanol, and 0.1 M lactic acid (2:2:1), and detected with a reagent (composed of aniline, diphenylamine, acetone, and phosphoric acid), glucose, galactose, mannose, and glucuronic acid are detected. A gas chromatographic analysis confirmed that at least (a) glucose, (b) galactose, (c) mannose, and (d) glucuronic acid are the main constitutional saccharides for the polysaccharides of the invention, and that the molar ratio of (a) glucose to (b) galactose to (c) mannose to (d) glucuronic acid is about 10:3–6:0.5–2:0.5–2.

A more detailed examination was made of the proportion of each saccharide component constituting the present polysaccharides. The polysaccharides were hydrolyzed with 2N sulfuric acid at 105° C. for 15 hours and neutralized with barium hydroxide, and the resulting hydrolyzates were analyzed by high performance liquid chromatography. This analysis shows that the ratio of glucose to galactose to mannose is 10:3–4:1–2.

The glucuronic acid content was determined by the following method:

The present polysaccharides were directly reduced with $NaBH_4$ to convert glucuronic acid to glucose, and thereafter, were hydrolyzed in the same condition as described above. The resulting hydrolyzates were analyzed by high performance liquid chromatography, and the glucuronic acid content was determined as an increment of the amount of glucose. This analysis shows that the molar ratio of (a):(b):(c):(d) is 10:3–4:1–2:1–2.

(8) Elemental Analysis

C: 40.63±1%; H: 6.74±1%; N: 0%; ash content: 1.07±0.8%

(9) Optional Rotation $[\alpha]_D^{27}$: +8.0 to +20.0 (C=0.33, aqueous solution)

(10) Other Characteristic Properties

Figure 7:
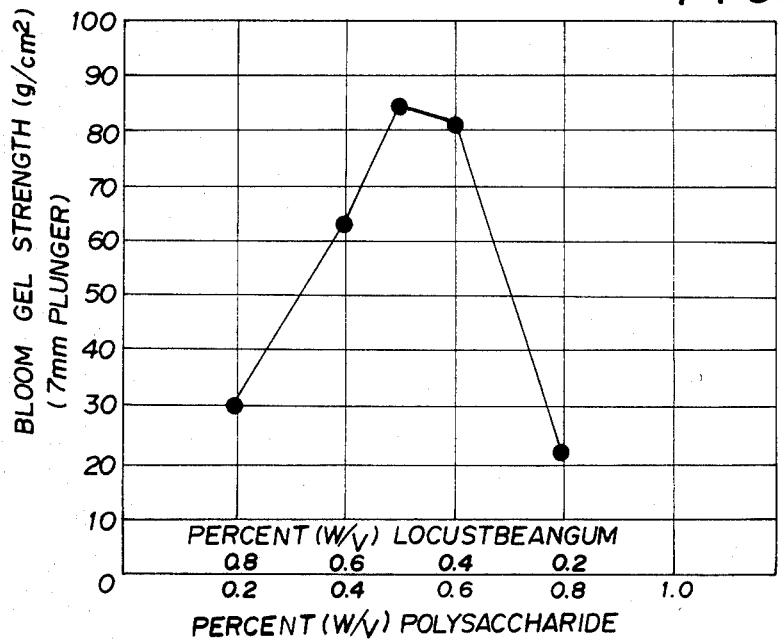
FIG. 7 is a graph showing the synergism of the polysaccharides of the invention with locust bean gum.

An aqueous solution of the present polysaccharides is mutually soluble with galactomannens, such as locust bean gum and guar gum, and have gelling characteristics or exhibit high viscosity. The synergism of the polysaccharides of the invention with locust bean gum is shown in FIG. 7.

(11) Molecular Weight (a) Viscometric Measurement

The intrinsic viscosity $[\eta]$ (as determined by means of an Ubbellohde viscometer; solvent: water) of the polysaccharides of the invention is from 60 to 80 deciliters per gram (dl/g). This value is used to calculate the molecular weight of the present polysaccharides according to Staudinger's equation. The molecular weight is from about $1.65 \times 10^7$ to $2.2 \times 10^7$.

(b) High Performance Liquid Chromatographic Measurement

This measurement was performed using a high performance liquid chromatography (HLC-802, Toyo Soda Kogyo Co., Ltd.) under the following conditions:
Filler: JSK G5000 PW (Toyo Soda Kogyo Co., Ltd.)
Column: 7.5 cm (inner diameter)×60 cm
Eluate 0.1 M Tris hydrochloric acid buffer (pH: 8.0)
Elusion Flow Rate: 0.95 ml/min
Detector: High sensitivity differential refractometer
Measuring Temperature: 25° C.
Standard Sample: Pulluran (produced by Hayashihara Co., Ltd.)

The molecular weight of the polysaccharides was $5 \times 10^5$ to $1.5 \times 10^6$.

(12) Melting Point

Turns black-brown at 190° C. and decomposes at 250° C..

(13) $^{13}C$ Nuclear Magnetic Resonance Spectrum

Figure 6:
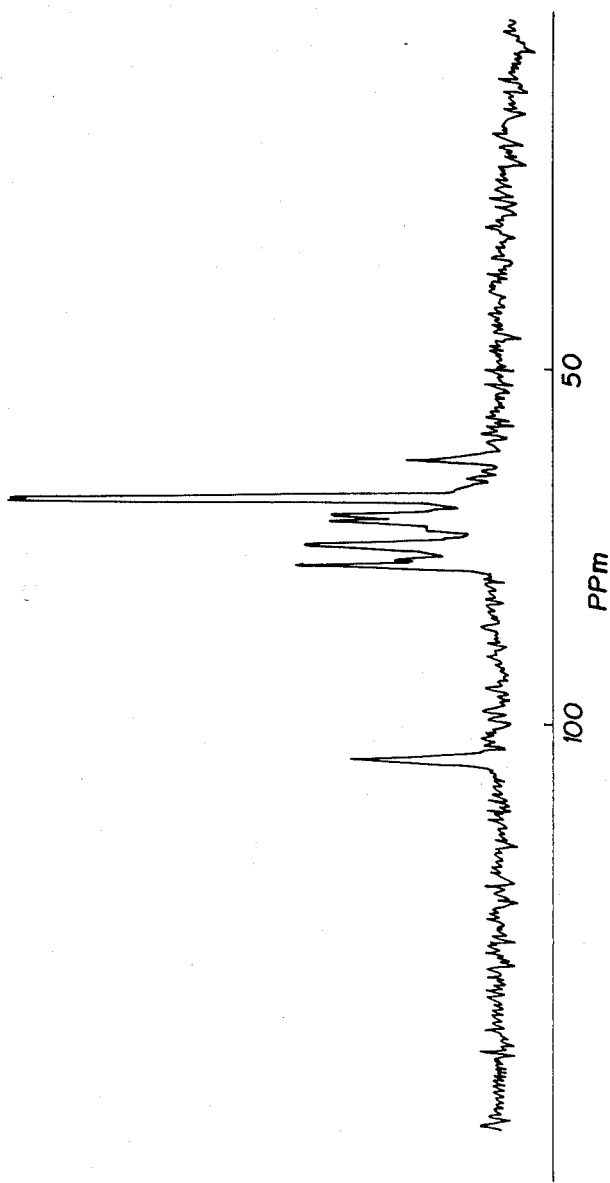
FIG. 6 is a $^{13}C$-nuclear magnetic resonance spectrum of the polysaccharides of the invention.

FIG. 6 shows the $^{13}C$ NMR spectrum of the polysaccharides of the invention (solvent: $D_2O$; tube: 10 millimeters; internal standard: dioxane).

Main peaks: 103.7 ppm; 76.9 ppm; 74.1 ppm; 70.7 ppm; 69.8 ppm; 62.1 ppm.

Polysaccharides composed mainly of glucose, galactose, mannose, and glucuronic acid which have heretofore been known include polysaccharides produced by Corynebacterium humiferum var. myxogenes (Japanese Patent Application Laid-Open No. 123890/1975), polysaccharides produced by Bacillus polymyxa 271 Nippon Nogeikagaku Kaishi (Journal of the Agricultural Chemical Society pan), 43, 780 (1969), and polysaccharides produced by Klebsiella pneumoniae (Japanese Patent Application Laid-Open No. 95792/1979). These known polysaccharides are clearly different from the polysaccharides of the invention with respect to types of constitutional saccharides, ratio, and viscosity characters. Thus, the polysaccharides produced by Corynebacterium humiferum var. myxogenes are different from the polysaccharides of the invention in that the former polysaccharides contain a larger amount of glucuronic acid. The polysaccharides produced by Bacillus polymyxa 271 are different from the polysaccharides of the invention in that the former polysaccharides have the composition ratio of glucose:galactose:mannose:glucuronic acid=3:1:3:2, which is clearly different from that of the polysaccharides of the invention. The polysaccharides produced by Klebsiella pneumoniae are different from the polysaccharides of the invention in that, in the former polysaccharides, the ratio of glucose:galactose:mannose:glucuronic acid is 26-32:19-23:30-37:15-.3-18.8, and they also contain 5.1 to 6.3% of an acetyl group and 4.5 to 5.4% of pyruvic acid.

In connection with heteropolysaccharides produced by bacteria belonging to acetic acid bacteria, it is reported in Can. J. Microbiol., 27, 599-603 (1981) that the spontaneous mutant of *Acetobacter xylinum* produces nitrogen-containing acidic heteropolysaccharides in which the ratio of glucose:rhamnose:mannose:glucuronic acid is 3:1:1:1, and the molar ratio of carbon atom to nitrogen atom is 165:1 (1.4% by weight as proteins). These polysaccharides are different from the polysaccharides of this invention which contain galactose as one of the main constitutional saccharides, rhamnose is not detected, and do not contain nitrogen. The polysaccharides of this invention are novel polysaccharides.

The polysaccharides of the invention are highly viscous polysaccharides produced by acetic acid bacteria which have been used from the prehistoric time for the production of vinegars, one of the most fundamental condiments of food and their safety has been confirmed. In view of their high viscosity and safety, they can be expected to be used as drugs (e.g., antitumor agents) as well as food thickeners and emulsion stabilizers in the field of food industry. In addition, it is possible to utilize the polysaccharides of this invention in industrial applications, e.g., as lubricants, covering agents, pastes, suspension aids, cosmetic base materials, additives for drilling mud, and thickeners for aqueous compositions for use in enhanced oil recovery.

The polysaccharides of the invention are highly viscous polysaccharides produced by acetic acid bacteria which have long been used in the brewing of vinegar and have been historically confirmed in their safety. In view of their safety and viscosity, they are very useful for use as additives, particularly thickeners and emulsion stabilizers in the food industry. That is, the polysaccharides of the invention can be added as thickeners or emulsion stabilizers in liquid and solid foodstuffs such as dressing, ice cream, jam, nectar, yogurt, chocolate, paste, sausage, syrup, jelly, candy, mayonnaise, whipping cream, ketchup, sauce, soup, beer, alcoholic drinks, soybean sauce, vinegar, pickles, etc.

The amount of the polysaccharides to be added to each foodstuff can be appropriately and optionally determined depending on the type of the foodstuff. Usually it is added within the range of from 0.01 to 20% by weight, based on the volume of the ultimate product.

In addition, the polysaccharides of the invention can be utilized in increasing the viscosity and permeability of flooding water which is used in the tertiary recovery of oil from oil fields by the chemical flooding method. In general, in the recovery of oil, the inner pressure in the reservoir decreases during operation, as a result of which only minor portions of the original oil in place can be recovered. For further recovery of oil, it is necessary to employ a mechanical method, e.g., pumping. Even by this mechanical method, however, only about 10 to 25% of the total oil in the reservoir can be recovered, and the major portion of oil still remains unrecovered.

In order to efficiently recover such oil remaining in the reservoirs, a number of secondary and tertiary recovery methods have been developed. These methods include the chemical flooding method in which water whose viscosity and permeability have been increased by addition of polysaccharides is introduced under pressure into the oil-bearing reservoirs to recover the oil. In general, it is a requirement for the viscous polymers used in the chemical flooding method to be stable against changes in temperature, salt concentration, and pH, and at the same time, to exhibit good fluid characteristics or injectivity. The polysaccharides of the invention exhibit high injectivity, even if they contain a high concentration of salts. For example, in the presence of from 5 to 10% salt, they exhibit high permeability, even for oil-bearing rock having a pore size as small as from 0.8 to 1.2 microns.

The polysaccharides of the invention can be used alone or in combination with known viscous polymers such as polyacrylamide and xanthan gum. The amount of polysaccharide being compounded is determined depending on the purpose for which it is used and the characteristics of oil-bearing rock. Usually, the present polysaccharide is added in an amount of from 0.001 to 5% by weight based on the weight of flooding water to prepare a viscous composition.

The following examples are given to illustrate the invention in greater detail.

EXAMPLE 1

A mixture of 0.1 gram of potassium phosphate, monobasic, 0.1 gram of potassium phosphate, dibasic, 0.25 gram of magnesium sulfate hepta-hydrate, 0.005 gram of ferric chloride, 2 grams of yeast extract, and 30 grams of sucrose was dissolved in 1 liter of distilled water to prepare a culture medium. In this way, 3 liters of culture medium was prepared. The culture medium was adjusted to pH 6.0, introduced into a 5-liter jar fermentor, and sterilized at 120° C. for 20 minutes.

*Acetobacter polysaccharogenes* MT-11-2 (FERM BP-112), which had been previously cultivated using a nutrient medium having the same composition as described above in Sakaguchi flask, was placed in the above-described jar fermentor and cultivated at a temperature of 30° C. and an aeration amount of 0.5 air volume per liquid volume per minute (VVM) for 96 hours. At the same time, the pH of the fermentation broth was 3.4, and the viscosity as determined by a Brookfield viscometer was 120 centipoises (cp).

Water was added to the fermentation broth to adjust the volume to 10 liters. The resulting solution was centrifuged at 10,000 revolutions per minute (rpm) for 20 minutes to separate microbial cells and solid materials. Upon gradual addition of 15 liters of ethanol, there was obtained a white and fibrous precipitate. The precipitate was collected, washed with acetone, and vacuum-dried. The amount of the thus-obtained white and fibrous crude polysaccharides was 22.5 grams (yield: 25%).

The above-obtained crude polysaccharides (20 grams) were again dissolved in 2 liters of water, and cetyltrimethylammonium bromide was added thereto to precipitate the polysaccharides as a complex material of the polysaccharides and cetyltrimethylammonium bromide. The complex material was fully washed with water and ethanol to remove excessive cetyltrimethylammonium bromide, and a saturated aqueous solution of sodium chloride was then added to the complex material to dissolve it therein. To the resulting solution was added a 3-fold amount of ethanol to precipitate the polysaccharides. The precipitate was separated, vacuum-dried and again dissolved in water. The thus-obtained solution was introduced into a cellophane tube for dialysis and dialyzed in flowing water for 3 days. Thereafter, a 3-fold amount of acetone was added to precipitate the polysaccharides. The precipitate was collected and vacuum-dried to obtain 18.5 grams of the purified polysaccharides.

EXAMPLE 2

A mixture of 0.1 gram of potassium phosphate, monobasic, 0.1 gram of potassium phosphate, dibasic, 0.25 gram of magnesium sulfate hepta-hydrate, 0.005 gram of ferric chloride, 2 grams of yeast extract, 5 grams of citric acid, and 25 grams of mannitol was dissolved in 1 liter of distilled water to prepare a culture medium. In this way, 3 liters of culture medium was prepared. The culture medium was adjusted to pH 6.0, introduced into a 5-liter jar fermentor, and sterilized at 120° C. for 20 minutes.

*Acetobacter polysaccharogenes* MT-11-2 (FERM BP-112), which had been previously cultivated using a nutrient medium having the same composition as described above in a Sakaguchi flask, was placed in the above-described jar fermentor and cultivated at a temperature of 30° C. and an acration amount of 0.5 VVM for 80 hours.

At the end of the time, the pH of the fermentation broth was 5.6, and the viscosity as determined by a Brookfield viscometer was 1,100 centipoises (cp).

The fermentation broth was treated in the same manner as in Example 1 to obtain 45 grams of crude polysaccharides (yield: 60%).

EXAMPLE 3

A mixture of 0.1 gram of potassium phosphate, monobasic, 0.1 gram of potassium phosphate, dibasic, 0.25 gram of magnesium sulfate hepta-hydrate, 1 gram of corn steep liquor, and 55 grams of waste molasses (containing 55% sucrose) was dissolved in 1 liter of distilled water to prepare a culture medium. In this way, 10 liters of culture medium was prepared. The culture medium was adjusted to pH 6.0, introduced into a 20-liter jar fermentor, and sterilized at 120° C. for 20 minutes.

*Acetobacter polysaccharogenes* MF-8 (FERM BP-113), which had been previously cultivated using a nutrient medium having the same composition as described above in a Sakaguchi flask, was placed in the above-described jar fermentor and cultivated at a temperature of 30° C. and an aeration amount of 0.5 VVM for 80 hours. During the cultivation, the pH was adjusted to about 6.0 by adding an aqueous solution of sodium hydroxide or an aqueous solution of hydrochloric acid. At the end of the time, the viscosity as determined by a Brookfield viscometer was 2,500 centipoises (cp).

The fermentation broth was treated in the same manner as in Example 1 to obtain 260 grams of crude polysaccharides (yield: 86%).

EXAMPLE 4

A mixture of 1 gram of potassium phosphate, monobasic, 1 gram of potassium phosphate, dibasic, 0.25 gram of magnesium hepta-hydrate, 2 grams of corn steep liquor, 2 grams of peptone, and 20 grams of glucose was dissolved in 1 liter of distilled water to prepare a culture medium. In this way, 10 liters of culture medium was prepared. The culture medium was adjusted to pH 6.0, introduced into a 20-liter jar fermentator, and sterilized at 120° C. for 20 minutes.

*Acetobacter polysaccharogenes* MF-8 (FERM BP-113), which has been previously cultivated using a nutrient medium having the same composition as described above in a Sakaguchi flask, was introduced in the above-described jar fermentor and cultivated at a temperature of 30° C. and an aeration amount of 0.5 VVM for 80 hours. During the cultivation, the pH was adjusted to about 5.0 by adding an aqueous solution of sodium hydroxide or an aqueous solution of hydrochloric acid. At the end of the time, the viscosity as determined by a Brookfield viscometer was 1,200 centipoises (cp).

The fermentation broth was treated in the same manner as in Example 1 to obtain 162 grams of crude polysaccharides (yield: 81.0%).

EXAMPLE 5

A mixture of 1 gram of potassium phosphate, monobasic, 1 gram of potassium phosphate, dibasic, 0.25 gram of magnesium sulfate hepta-hydrate, 0.09 gram of ferric chloride, 2 grams of yeast extract, 1 gram of corn steep liquor, 8 grams of succinic acid, and 30 grams of glycerol was dissolved in 1 liter of distilled water. In this way, 3 liters of culture medium was prepared. The culture medium was adjusted to pH 6.0, introduced into a 5-liter jar fermentor, and sterilized at 120° C. for 20 minutes.

*Acetobacter polysaccharogenes* MT-11-2 (FERM BP-112), which had been previously cultivated using a nutrient medium having the same composition as described above in a Sakaguchi flask, was introduced into the above-described jar fermentor and cultivated at a temperature of 28° C. and an aeration amount of 0.4 VVM for 96 hours. At the end of the time, the pH of the fermentation broth was 5.45, and the viscosity as determined by a Brookfield viscometer was 1,900 centipoises (cp).

The fermentation broth was treated in the same manner as in Example 1 to obtain 61.6 grams of crude polysaccharides (yield: 54%).

EXAMPLE 6

A mixture of 1 gram of potassium phosphate, monobasic, 2 grams of potassium phosphate, dibasic, 0.25 gram of magnesium sulfate hepta-hydrate, 2 grams of yeast extract, 1 gram of citric acid, and 30 grams of sucrose was dissolved in 1 liter of distilled water to prepare a culture medium. In this way, 3 liters of culture medium was prepared. The culture medium was adjusted to pH 6.0, introduced into a 5-liter jar fermentor, and sterilized at 120° C. for 20 minutes.

*Acetobacter pasteurianus* IFO 13751 (ATCC 23753), which had been previously cultivated using a culture medium having the same composition as described above in a Sakaguchi flask, was introduced into the above-described jar fermentor and cultivated at a temperature of 30° C. and an aeration amount of 0.5 air volume per liquid volume per minute (VVM) for 120 hours. During the cultivation, the pH was adjusted to about 6.0 using an aqueous solution of sodium hydroxide or an aqueous solution of hydrochloric acid. At the end of the time, the viscosity as determined by a Brookfield viscometer was 23 centipoises (cp).

The fermentation broth (3 liters) was treated in the same manner as in Example 1 to obtain 6.0 grams of purified polysaccharides (yield: 6.7%).

EXAMPLE 7

A mixture of 1 gram of potassium phosphate, monobasic, 2 grams of potassium phosphate, dibasic, 0.25 gram of magnesium sulfate hepta-hydrate, 2 grams of yeast extract, 1 gram of citric acid, and 30 grams of glucose was dissolved in 1 liter of distilled water to prepare a culture medium. In this way, 3 liters of culture medium was prepared. The culture medium was adjusted to pH 6.0, introduced into a 5-liter jar fermentor, and sterilized at 120° C. for 20 minutes.

*Gluconobacter capsulatus* IFO 3462(NRRL B-1225) which had been previously cultivated using a culture medium having the same composition as described above in a Sakaguchi flask, was introduced into the above-described jar fermentor and cultivated at a temperature of 30° C. and an aeration amount of 0.5 VVM for 240 hours. During the cultivation, the pH was adjusted to about 6.0 using an aqueous solution of sodium hydroxide or an aqueous solution of hydrochloric acid.

At the end of the time, the viscosity as determined by a Brookfield viscometer was 21 centipoises (cp).

The fermentation broth (3 liters) was treated in the same manner as in Example 1 to obtain 4.6 grams of purified polysaccharides (yield: 5.1%).

What is claimed is:

1. Highly viscous polysaccharides composed mainly of (a) glucose, (b) galactose, (c) mannose, and (d) glucuronic acid, the molar ratio of (a):(b):(c):(d) being 10:3–6:0.5–2:0.5–2.

2. The polysaccharides of claim 1, wherein the molar ratio of (a):(b):(c):(d) is 10:3–4:1–2:1–2.

3. The polysaccharide of claim 1 wherein the main repeating units of the polysaccharide has the following structure

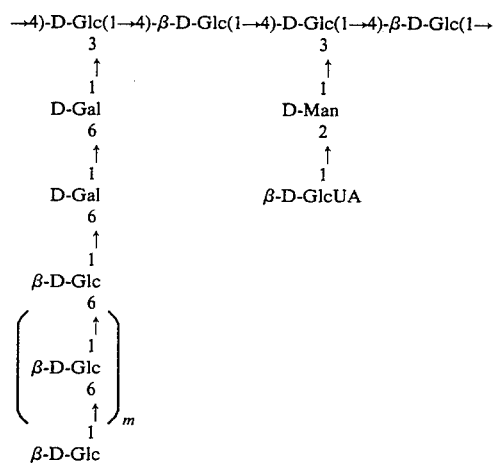

wherein m is 0 or 1, Glc is glucose, Gal is galactose, Man is mannose, and GlcUA is glucuronic acid.

* * * * *